US006635275B1

(12) United States Patent
Scott et al.

(10) Patent No.: US 6,635,275 B1
(45) Date of Patent: Oct. 21, 2003

(54) MODIFIED STARCH FILM COMPOSITIONS

(75) Inventors: Robert A. Scott, Sint Niklas (BE); Dominique Cadé, Colmar (FR); Xiongwei He, Andolsheim (FR)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 09/240,504

(22) Filed: Jan. 29, 1999

(51) Int. Cl.[7] ............................................... A61K 9/48
(52) U.S. Cl. ..................... 424/451; 424/400; 424/456; 424/463; 424/474; 424/475; 424/479
(58) Field of Search ................. 424/400, 451, 424/456, 463, 474, 475, 479; 264/301; 106/210, 206

(56) References Cited

U.S. PATENT DOCUMENTS

| 2,876,217 A | * | 3/1959 | Paschall | ................ | 260/233.3 |
| 3,378,546 A | * | 4/1968 | Tsuzuki | ................ | 536/111 |
| 3,505,110 A | * | 4/1970 | Kesler et al. | ................ | 127/29 |
| 4,026,986 A | * | 5/1977 | Christen et al. | ............ | 264/301 |
| 4,626,288 A | * | 12/1986 | Trzasko et al. | ............. | 106/210 |
| 5,224,989 A | | 7/1993 | Likarova | | |
| 5,525,368 A | * | 6/1996 | Rha et al. | ................... | 426/658 |

FOREIGN PATENT DOCUMENTS

| EP | 0606486 A1 | 7/1994 |
| JP | 5004914 | 1/1999 |

* cited by examiner

Primary Examiner—Thurman K. Page
Assistant Examiner—Charesse Evans
(74) Attorney, Agent, or Firm—Evan J. Federman

(57) ABSTRACT

The invention concerns compositions from modified starches, such as starch ethers or oxidized starch, more particularly hydroxpropylated starch (HPS) or hydroxylethylated starch (HES) for the use in pharmaceutical, veterinary, food, cosmetic or other products like films for wrapping food, aspics or jellies, preferably for predosed formulations like soft or hard capsules. The hard capsules obtained by the present invention with a conventional dipping molding process are similar to hard gelatine capsules (HGC).

3 Claims, No Drawings

MODIFIED STARCH FILM COMPOSITIONS

The invention concerns compositions from modified starches, such as starch ethers and oxidized starch, more particularly hydroxpropylated starch (HPS) and hydroxyethylated (HES) for the use in pharmaceutical, veterinary, food, cosmetic or other products like films for wrapping food, aspics or jellies, preferably for predosed formulations like soft or hard capsules. The hard capsules obtained by the present invention are similar to hard gelatine capsules (HGC).

A second embodiment of the invention is the use of the modified starch compositions for the manufacturing of hard capsules by conventional dip moulding process as normally used in the production of conventional hard gelatine capsules.

For the industrial manufacture of pharmaceutical capsules gelatine is most preferred for its gelling, film forming and surface active properties. The manufacture of hard gelatine capsules by dip moulding process exploits fully its gelling and film forming abilities. Such capsules are manufactured by dipping mould pins into a hot solution of gelatine, removing the pins from the gelatine solution, allowing the gelatine solution attached on pins to set by cooling, drying and stripping the so-formed shells from the pins. The setting of the solution on the mould pins after dipping is the critical step to obtain a uniform thickness of the capsule shell.

Attempts have been made to manufacture capsules with materials other than gelatine, notably with modified cellulose. Successful industrial examples are the capsules made of hydroxypropyl methylcellulose (HPMC). The HPMC capsules show several advantages over HGC. However, the raw material HPMC is significantly more expensive than gelatine.

Starch is another abundant natural polysaccharide which is renewable, biodegradable and of low cost. Because of the limited film forming ability and poor mechanical properties, the success in this field is more limited. A unique industrial example (U.S. Pat. No. 4,738,724) are starch capsules produced by injection moulding, but such capsules have a much higher shell thickness and a different shape which requires specific filling and closing equipment.

U.S. Pat. No. 4,026,986 describes the manufacture of HPS capsules by dip moulding process. However, due to the absence of setting ability of HPS solution, the dipping time is long (20 seconds), and therefore it did not result in commercial process.

Surprisingly, we found that the addition of a very small amount of a setting system, preferably consisting of hydrocolloids, most preferably polysaccharides, confers to HPS OR HES solution an appropriate setting ability with the result that hard HPS OR HES capsules can be manufactured by the dip moulding process of hard gelatine capsules under conventional process conditions.

The aim of the invention is therefore the provision of compositions based on HPS or HES for the use in pharmaceutical, veterinary, food, cosmetic or other products like films for wrapping food, aspics or jellies, preferably for containers for predosed formulations like soft or hard capsules and wherein the HPS or HES compositions have in aqueous solution a sufficient setting ability.

The first object of the invention is compositions based on HPS or HES to improve and adjust the mechanical properties of films for various applications.

We found that the addition of a plasticizer in the formulation can improve dramatically the HPS OR HES film flexibility. The plasticizer or mixture of plasticizers is selected from polyethylene glycol, glycerol, sorbitol, sucrose, corn syrup, fructose, dioctyl-sodium sulfosuccinate, triethyl citrate, tributyl citrate, 1,2-propylenglycol, mono-, di- or triacetates of glycerol, or natural gums. Preferred are glycerol, polyethylene glycol, propylene glycol, citrates and their combinations. The amount of plasticizer depends on the final application. For hard film formulations, such as for hard capsules, the plasticizer is contained in an amount of 0 to 20%, preferably 10–20%. A higher content, 20–30%, is preferred for soft film formulations, such as for soft capsules.

We found also that it is possible to further improve the film mechanical properties, by combining the HPS or HES with other hydrosoluble polymers or polysaccharides. The preferable examples are pectin, alginates, polyvinyl alcohol and high molecular weight polyethylene glycol.

The second object of the present invention is the achievement of an adequate setting ability of the HPS OR HES solution for process purpose.

The addition of a setting system, preferably based on polysaccharides, to HPS OR HES solutions enables the adaptation of specific and desired gelling properties for a selected process (film forming or dip moulding such as the production of hard HPS OR HES capsules by a conventional dipping process). For the production of hard capsules by dip moulding process, it is extremely important that the film forming HPS OR HES solution remaining on the mould pins after dipping is prohibited from flowing down the pins. Otherwise the obtained film will not have the desired uniform thickness.

With the compositions of the present invention we can produce hard HPS OR HES capsules with the same equipment and in the same range of process conditions as used for the production of conventional hard gelatine capsules. Furthermore capsules produced from compositions of the instant invention have the same dimensional specifications and allow the use of the existing filling machinery and do not require specific and new equipment for the filling process.

The HPS OR HES concentration in the dipping solution is in a range of 10 to 50%, preferably in the range of 20 to 40% by weight.

The setting system consists of a hydrocolloid or mixtures of hydrocolloids and may contain in addition cations and/or sequestering agents.

Suitable hydrocolloids or mixtures producing synergistic properties may be selected from natural seaweeds, natural seed gums, natural plant exudates, natural fruit extracts, biosynthetic gums, gelatines, biosynthetic processed starch or cellulosic materials, preferred are polysaccharides.

The preferred polysaccharides are alginates, agar gum, guar gum, locust bean gum (carob), carrageenan, tara gum, gum arabic, ghatti gum, Khaya grandifolia gum, tragacanth gum, karaya gum, pectin, arabian (araban), xanthan, gellan, starch, Konjac mannan, galactomannan, funoran, and other exocellular polysaccharides. Preferred are exocellular polysaccharides.

The preferred exocellular polysaccharides are xanthan, acetan, gellan, welan, rhamsan, furcelleran, succinoglycan, scleroglycan, schizophyllan, tamarind gum, curdlan, pullulan, and dextran.

The preferred hydrocolloids are kappa-carrageenan or gellan gum or combinations like xanthan with locust bean gum or xanthan with konjac mannan.

Among the setting systems mentioned above, the systems of kappa-carrageenan with cation and gellan gum with cation are specifically preferred. They produce high gel strength at low concentrations and have excellent compatibility with HPS.

The amount of the hydrocolloid is preferably in the range of 0.01 to 5% by weight and especially preferred 0.03 to 1.0% in the aqueous HPS OR HES solution.

The cations are preferably selected from $K^+$, $Na^+$, $Li^+$, $NH_4^+$, $Ca^{++}$ or $Mg^{++}$, for kappa-carrageenan is preferred $K^+$, $NH_4^+$ or $Ca^{++}$. The amount of cations is preferably less than 3%, especially 0.01 to 1% by weight in the aqueous HPS OR HES solution.

The preferred sequestering agents are ethylenediaminetetraacetic acid, acetic acid, boric acid, citric acid, edetic acid, gluconic acid, lactic acid, phosphoric acid, tartaric acid or salts thereof, methaphosphates, dihydroxyethylglycine, lecithin or beta cyclodextrin and combinations thereof. Especially preferred is ethylenediaminetetraacetic acid or salts thereof or citric acid or salts thereof. The amount is preferably less than 3%, especially 0.01 to 1% by weight of the dipping solution.

The inventive HPS OR HES compositions may contain in a further aspect additional pharmaceutically or food acceptable colouring agents in the range of from 0 to 10% based upon the weight of the film. The colouring agents may be selected from azo-, quinophthalone-, triphenylmethane-, xanthene- or indigoid dyes, iron oxides or hydroxides, titanium dioxide or natural dyes or mixtures thereof. Examples are patent blue V, acid brilliant green BS, red 2G, azorubine, ponceau 4R, amaranth, D+C red 33, D+C red 22, D+C red 26, D+C red 28, D+C yellow 10, yellow 2 G, FD+C yellow 5, FD+C yellow 6, FD+C red 3, FD+C red 40, FD+C blue 1, FD+C blue 2, FD+C green 3, brilliant black BN, carbon black, iron oxide black, iron oxide red, iron oxide yellow, titanium dioxide, riboflavin, carotenes, anthocyanines, turmeric, cochineal extract, clorophyllin, canthaxanthin, caramel, or betanin.

The HPS OR HES capsules of the invention may be coated with a suitable coating agent like cellulose acetate phthalate, polyvinyl acetate phthalate, methacrylic acid gelatines, hypromellose phthalate, hydroxypropylmethyl cellulose phthalate, hydroxyalkyl methyl cellulose phthalates or mixtures thereof to provide e.g. enteric properties.

The HPS OR HES capsules of the invention may be used for the production of containers for providing unit dosage forms for example for agrochemicals, seeds, herbs, foodstuffs, dyestuffs, pharmaceuticals, flavouring agents and the like.

The HPS OR HES capsules of the invention may be used where a release of filled product must occur at low temperature, such as at room temperature, which is not achievable with gelatine capsules.

The following examples and tests demonstrate the HPS OR HES capsule production and properties:

EXAMPLE 1

Production of HPS Capsules With 15% Plasticizer 1.5 kg of HPS powder is mixed with 25 g of kappa-carrageenan. To 3.21 kg of deionised water under stirring is added 0.5 g of potassium acetate (0.01% by weight in the solution) and 265 g of glycerol (5.3% in solution and 15% in capsule), followed by addition of the above mixture (30% of HPS and 0.5% of carrageenan in the solution). After the HPS is well dispersed, the dispersion is heated up to 90° C. under slow stirring, then held under strong stirring for 10 minutes to assure a good solubilisation of the components.

The HPS solution thus prepared is defoamed under slow stirring and then poured into a dipping dish of a pilot machine of conventional hard gelatine capsule production equipment. While keeping the dipping HPS solution at 60° C., natural transparent hard HPS capsules of size 0 were produced according to the conventional process with the same dimensional specifications to the conventional hard gelatine capsules.

Disintegration test results (according to USP XXIII 1995-<701>Disintegration):

| First leak time: | 21 seconds |
|---|---|
| Total disintegration time: | 263 seconds. |

EXAMPLE 2

Production of HPS Capsules With 10% PVA and 10% Plasticizer 1.4 kg of HPS powder is mixed with 10 g of kappa-carrageenan and 175 g of PVA (PVA has a viscosity of 33 cps at 4% and 20° C.). To 3.21 kg of deionised water under stirring is added 5 g of potassium acetate (0.10% by weight in the solution) and 175 g of glycerol (3.5% in solution and 10% in capsule), followed by addition of the above mixture (28% of HPS, 0.20% of carrageenan and 3.5% of PVA in solution). After the HPS is well dispersed, the dispersion is heated up to 90° C. under slow stirring, then held under strong stirring for 30 minutes to assure a good solubilisation of the components.

The HPS solution thus prepared is defoamed under slow stirring and then poured into a dipping dish of a pilot machine of conventional hard gelatine capsule production equipment. While keeping the dipping HPS solution at 60° C., natural transparent hard capsules of size 0 were produced according to the conventional process with the same dimensional specifications to the conventional hard gelatine capsules.

Disintegration test results:

| First leak time: | 51 seconds |
|---|---|
| Total disintegration time: | 225 seconds |

EXAMPLE 3

Production of HES Capsules With 10% Plasticizer 1.30 kg of HES powder is mixed with 4.00 g of gellan. To 3.55 kg of deionised water under stirring is added 5.00 g of potassium acetate (0.10% by weight in the solution), 2.00 g of ethylenediaminetetraacetic acid disodium salt (0.04%) and 145 g of glycerol (2.90% in solution and 10% in capsule), followed by addition of the above mixture (26.0% of HES and 0.08% of gellan in solution). After the HES is well dispersed, the dispersion is heated up to 98° C. under slow stirring, then held under strong stirring for 10 minutes to assure a good solubilisation of the components.

The HES solution thus prepared is defoamed under slow stirring and then poured into a dipping dish of a pilot machine of conventional hard gelatine capsule production equipment. While keeping the dipping HES solution at 60° C., natural transparent hard capsules of size 0 were produced according to the conventional process with the same dimensional specifications to the conventional hard gelatine capsules.

Disintegration test results:

| First leak time: | 28 seconds |
|---|---|
| Total disintegration time: | 443 seconds |

We claim:

1. A film former, comprising:
   a) a starch ether selected from the group consisting of hydroxypropylated starch, hydroxyethylated starch and mixtures thereof; and
   b) a film setting system comprising:
      i) from 0.01% to 10%, by weight, of a polysaccharide selected from the group consisting of alginates, agar gum, guar gum, locust bean gum (carob), carrageenan, tara gum, gum arabic, ghani gum, Khaya grandifolia gum, tragacanth gum, karaya gum, pectin, arabian (araban), xanthan, gellan, starch, Konjac mannan, galactomannan, funoran, acetan, welan, rhamsan, furcelleran, succinoglycan, scieroglycan, schizophyllan, tamarind gum, curdlan, pullulan, dextran and mixtures thereof;
      ii) from 0.001% to 5%, by weight, of a cation selected from the group consisting of K+, Na+, Li+, NH4+, Ca++ or Mg++ and mixtures thereof;
      iii) less than 3%, by weight, of a sequestering agent selected from the group consisting of ethylenediaminetetraacetic acid, acetic acid, boric acid, citric acid, edetic acid, gluconic acid, lactic acid, phosphoric acid, tartaric acid or salts thereof, methaphosphates, dihydroxyethylglycine, lecithin, beta cyclodextrin, salts thereof and mixtures thereof; and
      iv) from 2% to 12%, by weight, water.

2. A film former according to claim 1, wherein the film former comprises from 88% to 98% by weight of a starch ether.

3. A product comprising a film former wherein the film former comprises:
   a) a modified starch; and
   b) a film setting system comprising:
      i.) from 0.01% to 10%, by weight of a hydrocolloid selected from the group consisting of natural seaweeds, natural seed gums, natural plant exudates, natural fruit extracts, biosynthetic gums, biosynthetic processed starch, cellulosic materials, polysaccharides and mixtures thereof.
      ii.) from 0.001% to 5%, by weight, of a cation selected from the group consisting of K+, Na+, Li+, NH4+, Ca++ or Mg++ and mixtures thereof;
      iii.) less than 3%, by weight, of a sequestering agent selected from the group consisting of ethylenediaminetetraacetic acid, acetic acid, boric acid, citric acid, edetic acid, gluconic acid, lactic acid, phosphoric acid, tartaric acid or salts thereof, methaphosphates, dihydroxyethylglycine, lecithin, beta cyclodextrin, salts thereof and mixtures thereof; and
      iv.) from 2% to 12%, by weight, water.

* * * * *